United States Patent
Hover et al.

(10) Patent No.: US 6,296,645 B1
(45) Date of Patent: Oct. 2, 2001

(54) INTRAMEDULLARY NAIL WITH NON-METAL SPACERS

(75) Inventors: Anne Hover, Playa Del Rey, CA (US); Roy Sanders, Tampa, FL (US); Donald Martin Sturgeon, Wilmington, DE (US)

(73) Assignee: Depuy Orthopaedics, Inc., Warsaw, IN (US)

(*) Notice: Subject to any disclaimer, the term of this patent is extended or adjusted under 35 U.S.C. 154(b) by 0 days.

(21) Appl. No.: 09/289,324

(22) Filed: Apr. 9, 1999

(51) Int. Cl.[7] .................................................. A61B 17/56
(52) U.S. Cl. ........................................................ 606/62
(58) Field of Search .................................. 606/60, 62, 63, 606/64, 65, 69, 70

(56) References Cited

U.S. PATENT DOCUMENTS

| | | | |
|---|---|---|---|
| 2,136,471 | 11/1938 | Schneider | 128/92 |
| 2,987,062 | 6/1961 | Ellison | 128/92 |
| 3,272,204 | 9/1966 | Artandi et al. | 128/334 |
| 3,463,158 | 8/1969 | Schmitt et al. | 128/334 |
| 3,596,656 | 8/1971 | Kante | 128/92 |
| 3,636,956 | 1/1972 | Schneider | 128/335.5 |
| 3,739,773 | 6/1973 | Schmitt et al. | 128/92 |
| 3,892,649 | 7/1975 | Phillips et al. | 204/181 |
| 3,918,100 | 11/1975 | Shaw et al. | 3/1.9 |
| 4,146,936 | 4/1979 | Aoyagi et al. | 3/1.91 |
| 4,186,448 | 2/1980 | Brekke | 3/1.9 |
| 4,192,021 | 3/1980 | Deibig et al. | 3/1.9 |
| 4,279,249 | 7/1981 | Vert et al. | 128/92 |
| 4,280,233 | 7/1981 | Raab | 3/1.91 |
| 4,292,694 | 10/1981 | Koeneman | 3/1.91 |
| 4,338,926 | 7/1982 | Kummer et al. | 129/92 |
| 4,457,301 | 7/1984 | Walker | 128/92 |
| 4,550,449 | 11/1985 | Tunc | 623/16 |
| 4,612,923 | 9/1986 | Kronenthal | 128/92 |
| 4,655,203 | 4/1987 | Törmälä et al. | 128/92 |
| 4,733,654 | 3/1988 | Marino | 128/92 |
| 4,756,307 | 7/1988 | Crowninshield | 128/92 |
| 4,790,302 | 12/1988 | Colwill et al. | 128/92 |
| 4,851,008 | 7/1989 | Johnson | 623/16 |

(List continued on next page.)

FOREIGN PATENT DOCUMENTS

| | | |
|---|---|---|
| 1 949 923 | 4/1971 | (DE) . |
| 0 491 983A1 | 7/1992 | (EP) . |
| 2 710 835 | 4/1995 | (FR) . |
| 1692566 A1 | 11/1991 | (SU) . |

OTHER PUBLICATIONS

Brochure of Intramedullary Nail.
One Nail . . . , Diaphyseal Fractures.

(List continued on next page.)

*Primary Examiner*—Henry J. Recla
*Assistant Examiner*—Tan-Uyen T. Ho

(57) ABSTRACT

An intramedullary nail structure is formed with opposing dynamization windows, and spacers of a bioresorbable material are positioned within the dynamization windows. The dynamization windows are longer than they are wide. The spacers may be integrally formed as a single insert. The nail is used with a bone fastener such as a bone screw which is advanced transversely through the bone and into the spacer, preferably in a bicortical attachment with the bone. The bone fastener is smaller across than the dynamization windows, so each spacer spaces the bone fastener relative to its dynamization window. As the spacers resorb, stress (at least in one direction) is increasingly transmitted through the fracture site rather than through the intramedullary nail. The positioning of the bone fastener, the shape and size of the dynamization windows and spacers, and the material of the spacers all allow design control over the type and amount of dynamization seen at the fracture site. Also, because the bone fastener is smaller across than the dynamization windows and spacers, a larger error in placement of the bone fastener is permissible.

27 Claims, 5 Drawing Sheets

U.S. PATENT DOCUMENTS

| | | | |
|---|---|---|---|
| 4,863,475 | 9/1989 | Andersen et al. | 623/16 |
| 4,875,474 | 10/1989 | Border | 128/92 |
| 4,898,186 | 2/1990 | Ikada et al. | 606/62 |
| 4,911,153 | 3/1990 | Border | 606/98 |
| 4,919,666 | 4/1990 | Buchhorn et al. | 623/16 |
| 4,943,292 | 7/1990 | Foux | 606/70 |
| 4,968,317 | 11/1990 | Tormalla et al. | 606/77 |
| 4,973,333 | 11/1990 | Treharne | 606/77 |
| 5,057,110 | 10/1991 | Kranz et al. | 606/62 |
| 5,057,111 | 10/1991 | Park | 606/69 |
| 5,084,050 | 1/1992 | Draenert | 606/77 |
| 5,084,051 | 1/1992 | Tormala et al. | 606/77 |
| 5,108,399 | 4/1992 | Eitenmuller et al. | 606/77 |
| 5,127,913 | 7/1992 | Thomas, Jr. | 606/62 |
| 5,236,431 | 8/1993 | Gogolewski et al. | 606/72 |
| 5,275,601 | 1/1994 | Gogolewski et al. | 606/72 |
| 5,292,695 | 3/1994 | Galloway | 502/53 |
| 5,484,438 | 1/1996 | Pennig | 606/64 |
| 5,514,137 | 5/1996 | Coutts | 606/62 |
| 5,741,266 | 4/1998 | Moran et al. | 606/96 |
| 5,776,194 | 7/1998 | Mikol et al. | 623/16 |
| 5,792,400 | 8/1998 | Talja et al. | 264/103 |
| 5,810,821 | 9/1998 | Vandewalle | 606/65 |
| 5,868,746 | 2/1999 | Sarver et al. | 606/69 |
| 5,871,484 | 2/1999 | Spievack et al. | 606/60 |
| 5,895,390 | 4/1999 | Moran et al. | 606/96 |
| 5,928,267 | 7/1999 | Bonutti et al. | 606/216 |
| 5,935,127 * | 8/1999 | Border | 606/62 |
| 6,004,323 | 12/1999 | Park et al. | 606/61 |

OTHER PUBLICATIONS

System Introduction, *The Titanium Unreamed Tibial Nail System*.

Craig B. Ordway, Surgical Technique, *AIM Titanium Femoral Nail System*, New York, pp. 1–11.

Ferguson, Wyss and Pichora, "Finite Element Stress Analysis of a Hybrid Fracture Fixation Plate", Medical Engineering & Physics, vol. 18, No. 3, pp. 241–250, Apr., 1996.

Yeadon, Foux, Uhthoff, and Russell, "Influence of Axially Flexible Plates on Bone Healing: A Biomechanical Study in Canine Femora", CMBES 20 CCGB, pp. 34–35, 1994.

Simon, Ricci, and Di Cesare, "Bioresorbable Fracture Fixation in Orthopedics: a Comprehensive Review. Part II. Clinical Studies", American Journal of Orthopedics, pp. 754–762, Nov. 1997.

Kato, Latta, and Malinin, "The Weakest Link in the Bone—Plate—Fracture System: Changes with Time", Clinical and Laboratory Performance of Bone Plates, ASTM STP 1217, ed. by Harvey and Games, pp. 85–94, 1994.

Hazre and Lin, "Theoretical Strength Comparison of Bioabsorbable (PLLA) Plates and Conventional Stainless Steel and Titanium Plates Used in Internal Fracture Fixation", Clinical and Laboratory Performance of Bone Plates, ASTM STP 1217, ed. by Harvey and Games, pp. 53–64, 1994.

Räihä, "Biodegradable Implants as Intramedullary Nails. A Survey of Recent Studies and an Introduction to their Use," Clinical Materials, vol. 10, pp. 35–39, 1992.

Foux, Yeadon, and Uhthoff, "Improved Fracture Healing with Less Rigid Plates: A Biomechanical Study in Dogs", Clinical Orthopaedics and Related Research, ed. by Brighton, No. 339, pp. 232–245, 1997.

Biomet Inc., Vector Intertrochanteric Nail, Version Two, 18 pages, 1995. U.S.A.

Biomet Inc., Biomet Retrograde Femoral Nail, 6 pages, 1995. U.S.A.

Biomet Inc., Biomet Retrograde Femoral Nail Surgical Technique, 12 pages, 1995. U.S.A.

Biomet Inc., Uniflex® Humeral Nail Surgical Technique, 14 pages, 1997. U.S.A.

Biomet Inc., Uniflex® Femoral Nail Surgical Technique, 18 pages, 1996, U.S.A.

Biomet Inc., Titanium Femoral Interlocking Nail, 14 pages, 1995. U.S.A.

Biomet Inc., Vector Intertrochanteric Nail, Version One, 16 pages, 1995. U.S.A.

Biomet Inc., Uniflex™ Tibial Nail System, 4 pages, 1995. U.S.A.

Biomet Inc., Uniflex® Family Nailing System, 16 pages, 1995. U.S.A.

H. McKellop et al., Development and Clinical Performance Of A Reversible Titanium Alloy Femoral Intramedullary Nail, 15 pages, 1993. U.S.A.

\* cited by examiner

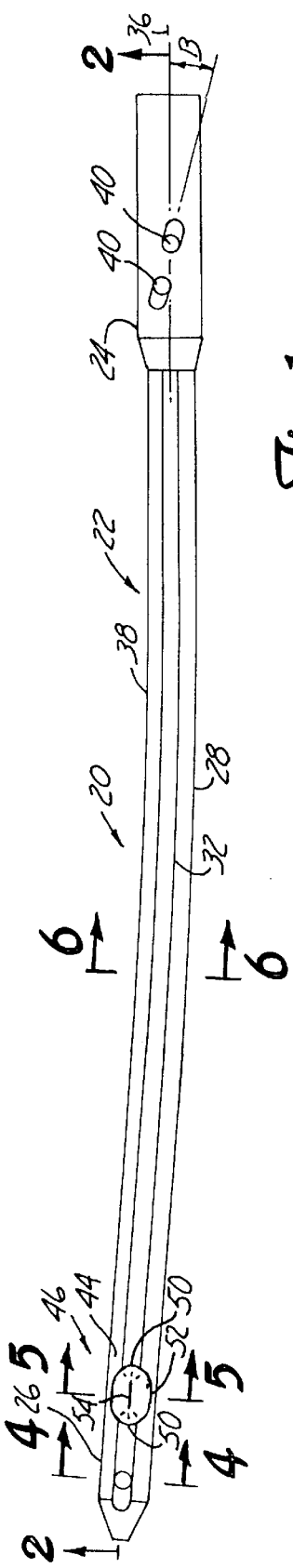

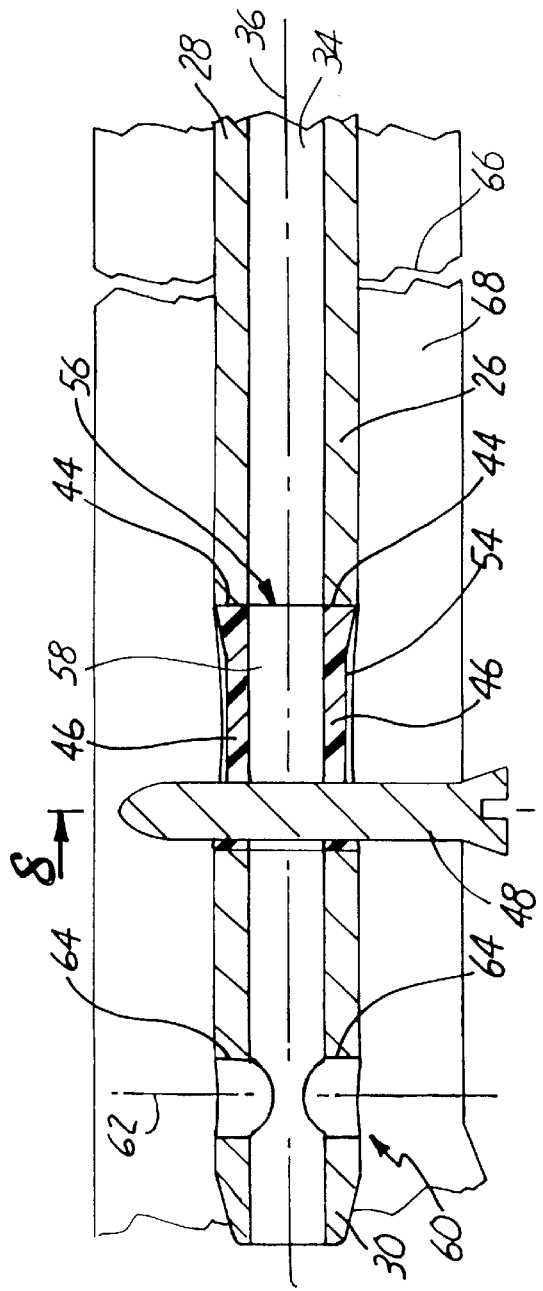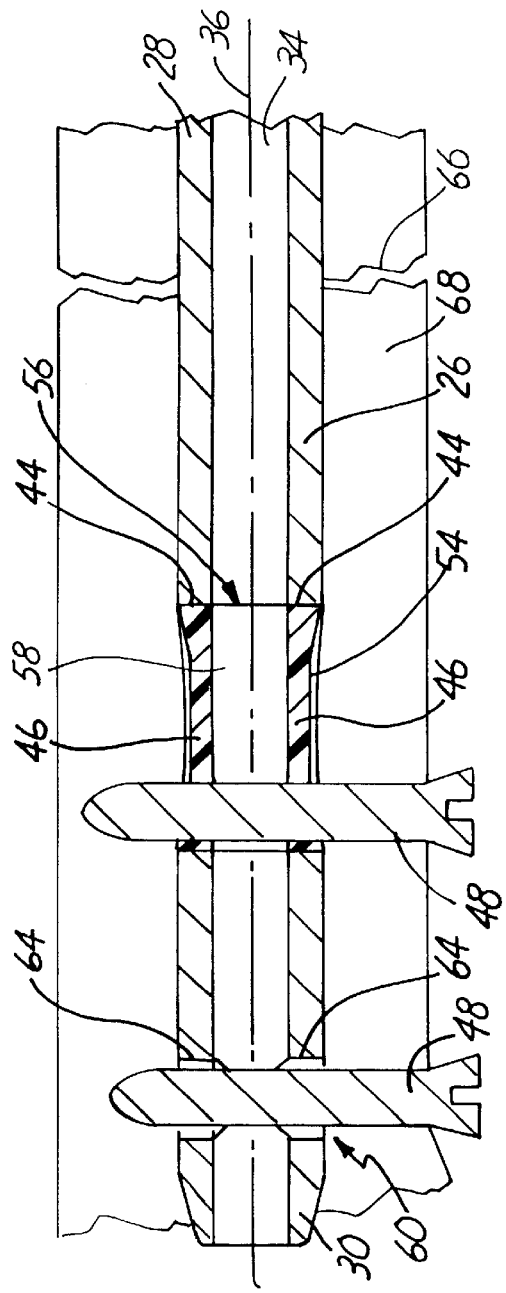

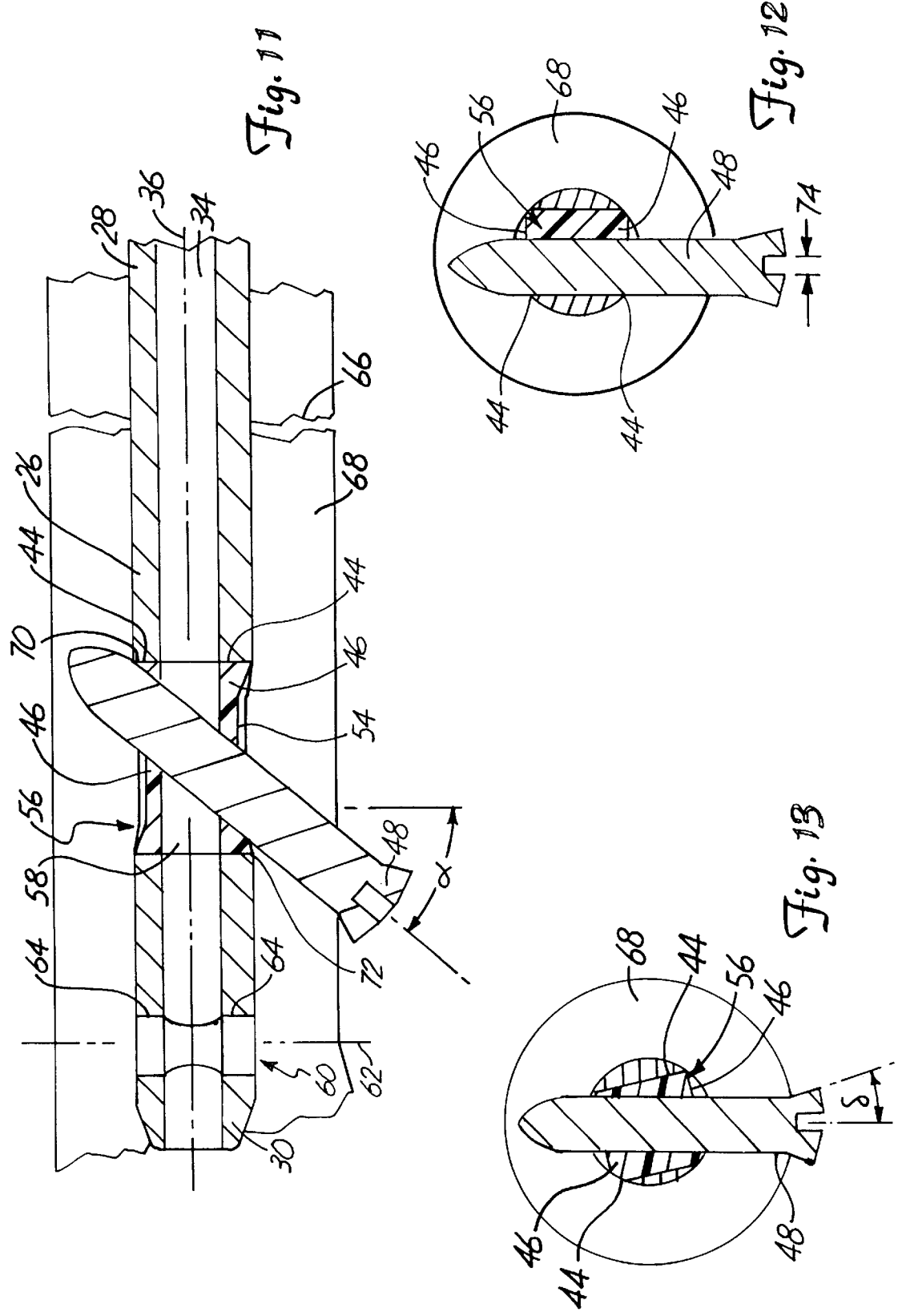

INTRAMEDULLARY NAIL WITH NON-METAL SPACERS

CROSS-REFERENCE TO RELATED APPLICATION(S)

None.

BACKGROUND OF THE INVENTION

The present invention relates to intramedullary nails used for treatment of a fracture of a bone having a medullary canal extending longitudinally within the bone, and particularly to the structure of the intramedullary nail and methods for anchoring the intramedullary nail with respect to one or more fragments of the fractured bone.

Intramedullary nails are used by orthopedic surgeons to treat fractures involving long bones such as the femur, humerus, tibia, fibula, etc. The medullary canal of the fractured bone is drilled out or otherwise opened from one end, and the intramedullary nail is longitudinally placed within the medullary canal to contact at least two fragments, i.e., such that the nail extends on both sides of the fracture. As used herein, the term "fragment" refers to a portion of a fractured bone regardless of whether the fracture is complete. When implanted, the nail strengthens and supports fragments of the fractured bone during healing of the fracture.

Various types of intramedullary nails are well known within the medical device arts, and several different methods have been used to attach the intramedullary nail within the bone. For instance, in U.S. Pat. No. 4,338,926 to Kummer et al., an intramedullary nail is disclosed which places a compressive force radially outward on the interior wall of the cortex structure surrounding the intramedullary nail. The compressive force secures the Kummer nail within the medullary canal of the fragments. Similarly, in U.S. Pat. No. 4,457,301 to Walker a flexible plastic core elements holds longitudinal pins of an intramedullary nail in place. In U.S. Pat. No. 5,514,137 to Coutts, cement is injected through a cannula in an intramedullary nail to secure the distal end of the intramedullary nail to the bone. Other intramedullary nail designs employ a more secure and mechanically positive attachment to the bone, such as through use of one or more bone fasteners which extend transversely to the longitudinal axis of the nail and through the cortex of the bone. The bone fastener is received within a receiving recess or through-hole within the intramedullary nail to secure the intramedullary nail relative to the bone fastener. In the transverse attachment, the receiving opening defines an axis which is at an angle to the longitudinal axis of the nail (90° and 45° angles are common), and the bone fastener is advanced on this receiving opening axis. U.S. Pat. No. 4,733,654 to Marino, U.S. Pat. No. 5,057,110 to Kranz et al., U.S. Pat. No. 5,127,913 to Thomas, Jr., U.S. Pat. No. 5,514,137 to Coutts (proximal end) and others disclose such a transverse bone fastener attachment in a bicortical attachment. U.S. Pat. No. 5,484,438 to Pennig shows a nail design with a recess which permits only unicortical attachment. The present invention particularly relates to intramedullary nails which use bone fasteners transversely through the cortex for attachment.

Problems may arise when attaching an intramedullary nail to a fragment with a bone fastener. It is occasionally difficult for the surgeon to properly align the bone fastener and/or a hole for the bone fastener with the receiving opening on the nail. Part of the error is simply due to difficulty in aligning the bone fastener with the receiving opening when the receiving opening is within the bone. Additionally, the nail may be slightly bent during insertion of the nail structure into the medullary canal. Such bending of the nail structure may be desired in some instances so the nail shape better matches the particular shape of the medullary canal for a particular patient. Regardless of whether intended or unintended, bending of the nail structure creates further alignment errors between the bone fastener and/or a hole for the bone fastener and the receiving opening on the nail. Four types of alignment errors can be identified: (a) in transverse displacement (e.g., when the axis of the bone fastener is in the same transverse plane as the receiving opening in the nail but does not intersect the axis of the nail), (b) in longitudinal displacement (i.e., when the bone fastener is at a different longitudinal location than the receiving opening in the nail), (c) in longitudinal angular misalignment (i.e., when the axis of the receiving opening and the axis of the bone fastener are at different angles relative to the longitudinal axis of the nail), and (d) in transverse angular misalignment (i.e., when the axis of the receiving opening and the axis of the bone fastener are in the same transverse plane but at different radial positions relative to the nail).

Various types of jigs have been proposed to reduce alignment errors, such as shown in U.S. Pat. No. 4,733,654 to Marino and U.S. Pat. No. 5,776,194 to Mikol et al. The jig may be temporarily attached to the proximal end of the nail to help align the bone fastener and/or the drill to the receiving opening in the nail. While such jigs are helpful, they become less reliable as distance from the proximal end of the nail increases, particularly if any bending of the intramedullary nail has occurred. Additional solutions are needed, especially for attaching the distal end of the intramedullary nail to a distal fragment.

A second method to reduce such alignment problems is to locate the receiving openings in-situ, such as through an x-ray or through the use of magnets as taught in U.S. Pat. No. 5,127,913 to Thomas, Jr. Such methods are not typically preferred by surgeons in as much as they require significant additional time and effort during the orthopedic surgery, to the detriment of the patient.

A third method to reduce such alignment problems is to drill the receiving opening into the intramedullary nail only after the nail is placed into the bone, allowing the receiving opening to be formed at a range of locations. Such in-situ drilling is taught in U.S. Pat. No. 5,057,110 to Kranz et al., wherein a tip section of the intramedullary nail is formed of a bioresorbable material. However, bioresorbable materials are not as strong as metals, leading to a product which is weaker than desired and has a weaker attachment than desired.

Further problems with intramedullary nails occur during placement of the intramedullary nail. For minimal damage to cortical tissue of the bone and most beneficial healing, both the hole that is drilled in the medullary canal for the nail and then the nail itself need to be precisely located and secured with respect to the medullary canal.

Additional problems with intramedullary nails occur due to the healing requirements of the bone with respect to the strength and rigidity of the nail. U.S. Pat. No. 4,756,307 to Crowninshield and U.S. Pat. No. 4,338,926 to Kummer et al. disclose intramedullary nails with bioresorbable portions to weaken the nail relative to the bone over time, but these nails forsake the use of a transverse bone fastener to achieve this benefit.

BRIEF SUMMARY OF THE INVENTION

The present invention is an intramedullary nail for treatment of a fracture of a bone by placement of the intramedullary nail within the medullary canal of the fractured bone. The nail structure is formed with at least one window in an exterior side, and a spacer of a non-metal materials positioned within the window. In one aspect of the invention, the non-metal spacer is formed of a bioresorbable material, and the window is a dynamization window. The nail is used with a bone fastener such as a bone screw which is advanced transversely through the bone and into the spacer, preferably in a bicortical attachment with the bone. The bone fastener is smaller across than the window, so the spacer spaces the bone fastener relative to the metal structure of the nail. The window may have a longitudinal length that is different from its width, while the bone fastener has a circular cross-section. Because the bone fastener is smaller across than the window and spacer, a larger error in placement of the bone fastener is permissible. Also, as the bioresorbable spacer resorbs, stress is increasingly transmitted through the fracture site rather than through the intramedullary nail. The positioning of the bone fastener, the shape and size of the window and spacer, and the material of the spacer all allow design control over the type and amount of dynamization seen at the fracture site.

BRIEF DESCRIPTION OF THE DRAWINGS

FIG. 1 is an elevational view of an intramedullary nail in accordance with the present invention.

FIG. 2 is a cross-sectional view taken along lines 2—2 in FIG. 1.

FIG. 3 is a cross-sectional view taken along lines 3—3 in FIG. 2.

FIG. 7 is a cross-sectional view of a distal end of the nail of FIGS. 1–6 in a first type of attachment to a bone.

FIG. 9 is a cross-sectional view of a distal end of the nail of FIGS. 1–6 in a second type of attachment to a bone.

FIG. 11 is a cross-sectional view of a distal end of the nail of FIGS. 1–6 in a fourth type of attachment to a bone.

FIG. 12 is a cross-sectional view similar to FIG. 8 showing a first type of permissible offset.

FIG. 13 is a cross-sectional view similar to FIG. 8 showing a second type of permissible offset.

Figure 4:
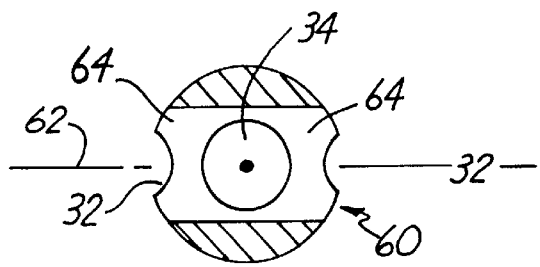
FIG. 4 is a cross-sectional view taken along lines 4—4 in FIGS. 1 and 3.

While the above-identified drawing figures set forth one or more preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

An intramedullary nail 20 according to the present invention includes a nail structure 22 with a proximal end 24, a distal end 26 and a shaft 28, with "proximal" and "distal" being defined in accordance with the direction the nail 20 is intended to be inserted into the bone. As known in the art, the dimensions of the proximal end 24, the distal end 26 and the shaft 28 may be selected based on the required strength of the nail and the intended use of the intramedullary nail. The nail 20 depicted in FIGS. 1–13 is generally sized and shaped for treating a fracture toward the middle of an otherwise healthy adult human femur. If desired, the nail 20 may be included in a kit having various sizes of nails to fit the femurs of variously sized patients, and/or having various sizes of nails to fit various types of femoral bone conditions or various types of femoral fractures, and/or further having various sizes of nails to fit various other bones. For instance, the length of the femoral nail 20 shown may be selected as needed between about 10 and 20 inches.

The distal end 26 may include a tip 30 having for instance a conical or partially conical profile. The conical profile of the tip 30 aids in inserting the nail 20 into the medullary canal. The shaft 28 may be generally of constant diameter. The proximal end 24 may include a portion of larger diameter than the shaft 28.

Figure 5:
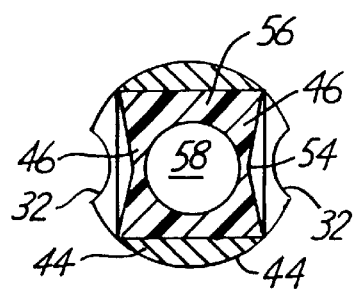
FIG. 5 is a cross-sectional view taken along lines 5—5 in FIGS. 1 and 3.
Figure 6:
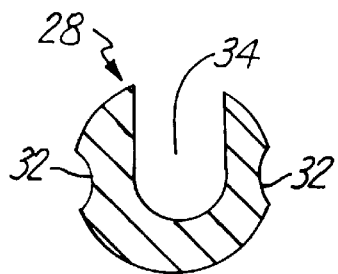
FIG. 6 is a cross-sectional view taken along lines 6—6 in FIGS. 1 and 3.

As shown in FIGS. 4–6 and known in the art, the nail 20 has an overall cross-sectional shape selected based upon the intended use. For a femoral nail 20, the cross-sectional shape may be generally circular, to match the generally circular cross-sectional shape of the medullary canal of a healthy femur. For instance, the shaft 28 may be generally formed with an outside diameter of 0.394 inches.

As best shown in FIGS. 1, 4 and 6, shallow longitudinal recesses 32 may be formed into the outside surface of the shaft 28. These longitudinal recesses 32 help to increase blood supply through the endosteum of the bone and to the fracture site during healing. Other cross-sectional shapes can be alternatively used for particular purposes or to better match the cross-sectional shape of the medullary canal of the particular bone being treated.

A cannula 34 preferably extends the length of the nail 20. The cannula 34 facilitates insertion and alignment of the nail 20 within the medullary canal. The cannula 34 may be formed at each of the ends 24, 26 by drilling along the longitudinal axis 36 of the nail 20. In the shaft 28 of the nail 20, the cannula 34 may be formed by cutting into the nail 20 from one of the sides. Alternatively, the cannula 34 may be formed by drilling longitudinally the entire length of the nail 20, which would result in a shaft 28 which encloses the cannula 34. Because the nail length is great compared with the nail width, it is generally easier to fabricate the cannula 34 by cutting laterally through the side of the shaft 28 than by drilling the length of the nail 20.

The cannula 34 receives a guide wire (not shown) during insertion of the nail 20 into the medullary canal. The guide wire has to be thick enough to provide the requisite strength and rigidity for placement into the bone, and the cannula 34 must be large enough to receive the guide wire and permit longitudinal travel of the nail 20 along the guide wire. Conversely, because a larger cannula 34 detracts from the strength of the nail 20, the cannula 34 should be as small as required for travel over the guide wire. The preferred guide wire is circular in cross-section, and as shown in FIGS. 4–6 the preferred cannula 34 generally matches this circular cross-section. For instance, the cannula 34 may be about 0.156 inches in diameter. With a shaft 28 of 0.394 inch (10 mm) diameter, this cannula 34 leaves a wall thickness for the shaft 28 of about 0.118 inches.

The preferred nail 20 includes a large radius bend 38 in the shaft 28, generally intended to match the anterior-posterior bend of a healthy femur. The bend 38 may have a large radius in relation to the length of the nail 20, such as a bend with a radius of 2 to 10 times the length of the nail 20. The curvature of the bend 38 may be applied over only a central portion of the shaft 28, leaving the proximal end 24 and distal end 26 straight. For instance, the bend 38 may be applied over a central 5 to 13 inches of the nail 20, depending on nail length.

Other than the cannula 34 being open from only one side of the shaft 28, the nail 20 is preferably symmetrical about a bisecting anterior-posterior plane. This allows the nail 20 to be used in either the right or left femur while still maintaining the bend 38 appropriate for the curvature of the femur.

The nail structure 22 is formed of a structurally strong biocompatible material as known in the art. For instance, the nail structure 22 can be formed of a single piece of metal, with the preferred metal being titanium, such as a Ti-6AL-4V ELI titanium per ASTM F-136.

The proximal end 24 is preferably formed with one or more through-holes 40 to facilitate attachment to a proximal bone fragment. For instance, the proximal end 24 may include two holes 40 which intersect each other. As best shown in FIG. 2, each of these holes 40 preferably extends at an angle $\alpha$ relative to the longitudinal axis 36 of the nail structure 22, with the preferred angle $\alpha$ being about 46°. Both the holes 40 preferably extend at an anteversion angle $\beta$ of about 15°, posteriorly (downward as shown in FIG. 2) on the proximal side and anteriorly (upward as shown in FIG. 2) on the distal side. These holes 40 allow attachment to a femoral fragment by bicortical attachment and with either antegrade fixation (i.e., through the trochanter) or reconstruction fixation (i.e., into the femoral head) as selected by the orthopedic surgeon. Alternatively or in conjunction with the through-holes 40, one or more recesses or cavities (not shown) may be provided in the proximal end 24 to permit unicortical attachment of the proximal end 24.

The proximal end 24 of the nail structure 22 may further include structure to facilitate attachment of a drilling or aligning jig (not shown) as known in the art for placement of bone fasteners relative to the nail 20. For instance, a proximal opening 42 aligned along the longitudinal axis 36 may be used to receive an end of a jig in a mating relationship. Workers skilled in the art will appreciate that numerous other structures could be equivalently used to temporarily hold the jig relative to the nail 20.

The distal end 26 of the nail structure 22 includes at least one dynamization window 44 through an external surface, with a spacer 46 in the dynamization window 44. The term "window" as used herein refers to an opening on an exterior surface of the nail 20. These windows 44 are referred to as "dynamization" windows because, when used in conjunction with a properly dimenisioned bone fastener (shown in FIGS. 7–13) and with a spacer 46 formed of a bioresorbable material, the proportion of stress carried by the nail 20 relative to stress carried by the healing bone across the fracture site dynamically changes as a function of time.

If desired, a single dynamization window or cavity may be provided, which would permit only unicortical attachment. In the preferred embodiment, two dynamization windows 44 are provided on opposite sides of the nail 20, with each dynamization window 44 extending entirely through the side wall of the nail 20 to permit communication with the cannula 34. After removal of the guide wire from the cannula 34, the dynamization windows 44 permit bi-cortical attachment by inserting a bone fastener through the cortex on one side of the nail 20, "in" one dynamization window 44, "out" the other dynamization window 44, and through the cortex on the other side of the nail 20. While the preferred embodiment includes only one set of dynamization windows 44, additional dynamization windows may be located at other longitudinal locations of the nail 20, including the proximal end 24 and the shaft 28 as well as the distal end 26. Any additional dynamization windows may either be single dynamization windows permitting unicortical attachment or opposing sets permitting bicortical attachment. Any additional dynamization windows may either be perpendicular to the bisecting plane or at other angles through the nail 20.

In the preferred embodiment, the dynamization windows 44 are aligned on opposite sides of the nail 20 at the same longitudinal location. With this configuration, both dynamization windows 44 may be simultaneously formed by a single cutting tool advanced through the nail 20 in a direction perpendicular to the bisecting plane. Alternatively, two dynamization windows may be longitudinally (and/or radially) offset with respect to each other and still permit bicortical attachment, provided they sufficiently overlap to permit the bone fastener to simultaneously pass through both windows.

A spacer 46 is placed in each dynamization window 44. During use of the nail 20 as shown in FIGS. 7–13, a bone fastener 48 is positioned into the dynamization window 44, and the spacer 46 spaces the bone fastener 48 relative to the nail structure 22 defining the dynamization window 44. Force is transmitted between the nail structure 22 and the bone fastener 48 primarily as a compressive load on a portion of the spacer 46.

Each spacer 46 is formed of a non-metal material, and preferably of a bioresorbable material. The term "bioresorbable" as used herein refers to any biocompatible material which dissolves or degrades over time after implantation into the human body. Among others, possible bioresorbable materials include polymers and copolymers glycolic acid, lactic acid, aminocaproic acid, lactides, desoxazon, hydroxybutric acid, hydroxyvaleric acid, hydroxymethacrylate, peptides, polyesters of succinic acid and cross-linked hyaluronic acid, or even a biologically absorbable hydroxyapatite or tricalcium phosphate. The preferred bioresorbable material is a polylactic acid ("PLA"), which provides a strong material for the spacers 46. The compressibility of the PLA material showing little change over the first few weeks of implantation, but then increases linearly over the next few months until resorption to the point where the material will no longer support a load. With the preferred PLA material, full resorption will typically occur within about two to five years.

The dynamization windows 44 and the spacers 46 are shaped based on the required strength and the desired dynamization characteristics for the nail 20. In the preferred embodiment as shown in FIGS. 1 and 3, both the first and second dynamization windows 44 and spacers 46 have circular ends 50 and a rectangular central section 52, and the spacers 46 fill the dynamization windows 44 in length and width. As will be further explained with reference to FIGS. 7–13, this shape provides substantial longitudinal dynamization flexibility while still providing adequate strength for the nail 20 at the dynamization windows 44. In the 0.394 inch (10 mm) OD nail 20 and for use with 0.177 inch (4.5 mm) OD bone screws 48, each end 50 may have a circular radius of 0.124 inches, with the central section 52 being 0.345 inches in length and 0.248 inches in width, for a total dynamization window length of 0.611 inches. Alternatively each spacer may not completely fill its dynamization window, such as by not being either full width or full length (which controls whether force transmitted through the spacer is in compression, in tension or in shear), or by having a central opening through each spacer.

As best shown in cross-sectional views of FIGS. 2 and 5, each spacer 46 has an exposed surface which preferably has a shallow groove 54 in the center. The groove 54 may provide a "V" shape to the exposed surface of the central section 52 of the spacer 46, while the exposed surface of the ends 50 of the spacer 46 may be conical. In the preferred embodiment shown, the groove 54 is about 0.04 inches (1 mm) deeper than the edges of the spacer 46. During surgical implantation of the bone fastener 48 into the nail 20, the groove 54 assists in directing the guide pin/drill/bone fastener toward the center of the spacer 46. Workers skilled in the art will appreciate that numerous alternative surface contours may be selected for one or both spacers 46 which still provide a generally sloped surface directing the guide pin/drill/bone fastener inward toward a center of each spacer 46.

In the preferred embodiment as best shown in FIG. 5, the two opposing spacers 46 are formed as a single insert 56. For instance, with a 0.394 inch (10 mm) OD nail 20, the insert 56 may have an overall thickness of about 0.286 inches (7.3 mm). Alternatively, each spacer 46 may be separately formed.

A cannula 58 is formed in the insert 56 to correspond with the cannula 34 of the nail structure 22, such that the two spacers 46 are defined on opposing sides of the cannula 58. With the center of the groove 54 on the outside and the cannula 58 toward the inside, the center of each spacer 46 may be quite thin. For instance, with a cannula 58 of about 0.156 inches (3.9 mm) in diameter, the center of each spacer 46 may be only about 0.025 inches (0.6 mm) thick.

As an alternative to the groove 54, the spacer 46 may include an exposed surface which is planar. Depending upon the material of the spacer 46 and the thickness of the spacer 46 relative to the cannula 58, the center of the spacer 46 may be resiliently deflected or deformed inward under pressure. For instance, the push force placed on the spacer 46 by the guide pin, drill and/or bone fastener during insertion through the spacer 46 may cause the center of the spacer 46 to resiliently deform, such that an exposed surface which was planar as manufactured provides a sloping profile which assists in directing the guide pin/drill/bone fastener toward the center of the spacer 46.

The preferred bioresorbable material is commercially available such as in about 150 in$^3$ blocks. The insert 56 may be formed by cutting the bioresorbable material to ⅝inch by ⅝inch by 3 inch portions, which may then be further fabricated to the shape of the insert 56 by CNC. The cannula 58 is preferably drilled into the insert 56 prior to insertion of the insert 56 into the nail 20, although the cannula 58 may alternatively be drilled after placing the insert 56 into the nail 20, either simultaneously with or after formation of the cannula 34 through the nail structure 22.

The insert 56 preferably fits into the dynamization windows 44 with a press fit. The insert 56 is pressed in the nail 20 until it aligns centrally within the nail 20. Initial results have indicated that several hundreds of pounds of press force is required to press the preferred insert 56 into the windows 44 of the preferred nail structure 22. During the surgery, the insert 56 can be drilled through with a push force which is at least an order of magnitude less than the press force, and the press fit amply secures the insert 56 into the nail 20.

Workers skilled in the art will appreciate that there are many other ways to attach the spacers 46 into the dynamization windows 44. Various recesses or protrusions on the spacers 46 and/or in the nail structure 22 may provide a higher pull strength or facilitate a positively secured attachment of the spacers 46 to the nail structure 22.

Attachment of the spacers 46 into the dynamization windows 44 does not have to be performed as a manufacturing step. Alternatively, the surgeon may attach the spacers 46 into the dynamization windows 44 as a preparatory step during surgery, and the nail structure 22 and spacers 46 may be appropriately modified to facilitate placement of the spacers 46 into the dynamization windows 44 by the surgeon. For instance, the insert 56 and dynamization windows 44 may have a smaller amount of interference to enable the surgeon the press the insert 56 into the nail structure 22 by hand. Alternatively, the surgeon may be provided with a mechanical press to facilitate pressing the insert 56 into the nail structure 22. If desired, a lubricant may be utilized to facilitate the press fit. The lubricant used may be volatile, so the insert 56 becomes tightly secured into the nail structure 22 after the lubricant evaporates. As another alternative, the insert 56 and the dynamization windows may be sized with a slight clearance and be adhesively secured. Any lubricant or adhesive should be biocompatible so as to not create complications in the healing process.

Attachment of the insert 56 into the dynamization windows 44 by the surgeon allows several further advantages. For instance, a single nail structure 22 may be provided as part of a kit which includes a plurality of inserts 56 having different properties. The different inserts 56 provided may have different mechanical properties, such as different hardnesses, different rates of absorption, etc., allowing the surgeon the flexibility to match the insert 56 used with the particular healing modality desired by the surgeon.

The non-metallic spacers 46 may also include one or more active agents to promote effective healing. For instance, the non-metal material of the spacers 46 may include one or more antibiotics such as gentamicin, methicillin, penicillin, etc. The non-metal material of the insert 56 may also include other active agents, such a one or more of a transforming growth factor—beta 1, a recombinant human bone morphogenetic protein –2, etc. If provided as part of a kit, different inserts 56 may be provided each with a different active agent or a different amount of active agent, so the surgeon can select the type and amount of active agent used for the particular surgery.

Another advantage of attachment of the insert 56 into the dynamization windows by the surgeon is that the insert 56 may be handled in a different environment from the nail structure 22. For instance, the insert 56 may be maintained in a particular thermal condition (e.g., refrigerated or frozen), or in a sealed container (e.g., sealed from air, sealed from humidity, etc.) until immediately prior to insertion into the dynamization windows 44 and immediately prior to implantation into the fractured bone. The controlled environment of the insert 56 may have beneficial results in physical properties (e.g., preventing dissipation or dilution of an active agent, etc.) or in mechanical properties (e.g., increased hardness, different size due to thermal expansion, etc.) of the insert 56 upon implantation.

The distal end 26 of the preferred nail 20 preferably includes a non-dynamic through-hole 60. The through-hole 60 has an axis 62 which is preferably perpendicular to the anterior-posterior plane and intersecting the longitudinal axis 36 of the nail 20. The through-hole 60 defines a first window 64 into the cannula 34 and a second window 64 out of the cannula 34 at the opposite side of the nail 20. Each window 64 may be circular in cross-section, and both windows 64 may be defined with a single drilling operation. The size and shape of the windows 64 are selected based on the intended bone fasteners to be used. For instance, both windows 64 may be circular with a 0.217 inch diameter. For bi-cortical attachment of the distal end 26 of the nail structure 22 using the through-hole 60, a bone fastener 48 is advanced through the through-hole 60, i.e., through both windows 64. While the preferred embodiment includes only one set of non-dynamization windows 64, additional non-dynamization windows 64 may be located at other longitudinal locations of the nail 20, including the proximal end 24 and the shaft 28 as well as the distal end 26. Any additional non-dynamization windows may either be single windows permitting unicortical attachment or opposing sets permitting bicortical attachment. Any additional non-dynamization windows may either be perpendicular to the bisecting plane or at other angles through the nail 20.

The bone fasteners 48 used with the nail 20 may be for instance bone pins or bone screws, sized and shaped as appropriate for the site of implantation. Each bone fastener 48 may be directly implanted into the cortex, or a hole may be drilled or otherwise opened in the cortex prior to placement of the bone fastener 48. The bone pin or bone screw may be solid, or may be cannulated such as for implantation over a guide pin. In the preferred embodiment, the distal through-hole 60 is sized to receive 0.177 inch (4.5 mm) outside diameter bone screws, and the dynamization windows 44 and spacers 46 are sized appropriately for 0.177 inch (4.5 mm) outside diameter bone screws. The proximal through-holes 40 as preferably sized appropriately for 0.256 inch (6.5 mm) outside diameter bone screws. Other types of bone fasteners may be alternatively used at the option of the orthopedic surgeon.

Figure 8:
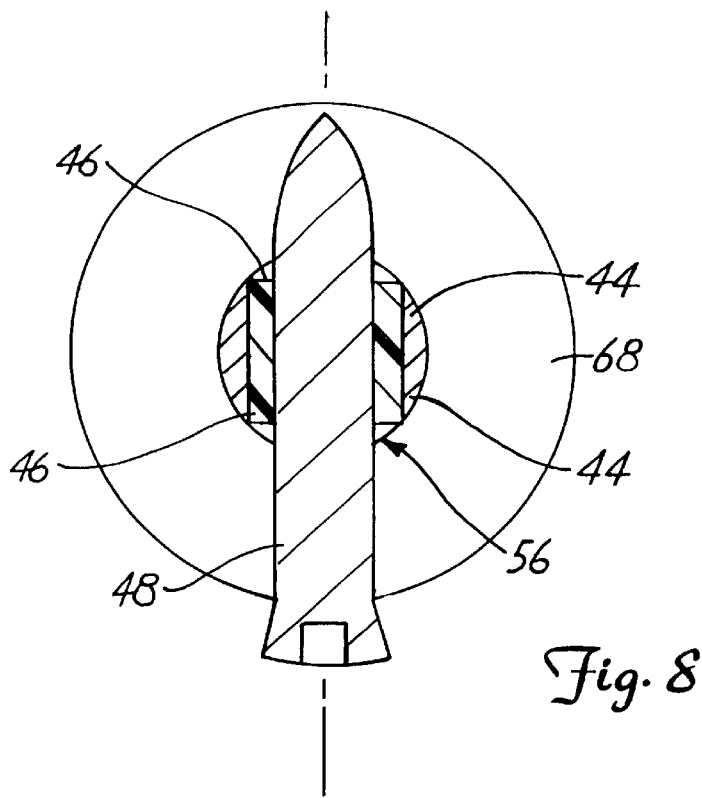
FIG. 8 is a cross-sectional view taken along lines 8—8 in FIG. 7.

FIGS. 7–13 show various attachment configurations for the nail 20 of the present invention. FIGS. 7 and 8 show a bicortical attachment with a single bone screw 48 positioned at the distal end of the two dynamization windows 44, which can be characterized as an "initial dynamic" locking position. Attached in this position, the nail 20 provides only compressive dynamization across the fracture site 66, as follows. The bioresorbable spacer 46 can be thought of as a compression spring with a time-varying spring constant, positioned within a substantially incompressible nail structure 22. In the attachment shown in FIGS. 7 and 8, substantially the entire length of the "spring" is on the proximal side of the bone fastener 48. Very little force is transmitted through the nail 20 until the bone is loaded. When the fractured bone is loaded in compression, the compressive load is carried across the fracture site 66 by the nail shaft 28 and then through the proximal length of the spacer 46, and then to the bone fastener 48 and distal fragment 68. Initially on implantation, the bioresorbable spacer 46 is very rigid and hard, and substantially incompressible like the nail structure 22. The nail 20 will carry substantially all of the compressive force, and none of the compressive force will be carried across the fracture site 66.

After the bone begins healing, such as after several weeks, the bioresorbable material begins to deteriorate. This increases the compressibility (lowers the spring constant) of the bioresorbable material in the dynamization window 44. In this condition, when a compressive stress is placed across the fracture site 66, the proximal side of the spacer 46 will compress slightly under the load. Because of this slight compression, significant amounts of the compressive stress will be carried by the healing bone as well as by the nail 20.

As the bioresorable material further deteriorates, the proportion of stress carried by the nail 20 relative to stress carried by the healing bone continues to decrease. The healing bone continues to be dynamized, until substantially all compressive stresses placed on the bone are carried across the fracture site 66 rather than by the nail 20.

Most of the stresses carried by the bone are compressive stresses rather than tensile stresses. Nonetheless, in contrast to the compressive dynamization, consider the path of tensile stress placed on the bone when the nail 20 is attached as shown in FIGS. 7 and 8. When the bone is loaded in tension, the tensile stress is carried across the fracture site 66 by the nail shaft 28 and then around to the distal side of the dynamization window 44 by the nail structure 22, then transferred as a compressive stress through only a small distal length of the spacer 46, and then to the bone fastener 48 and distal fragment 68. Because the bone fastener 48 is quite close to the distal end of the dynamization window 44, there is a very short length of bioresorbable material to undergo compression, and there is very little give in the sort distal length of bioresorbable material regardless of the amount of deterioration. Tensile stresses placed across the fracture site 66 are almost entirely borne by the nail 20, regardless of deterioration of the bioresorbable spacer 46.

FIG. 9 shows an alternative attachment of the nail 20, which can be either a "static" locking position or a "delayed dynamic" locking position depending upon screw removal, In this static locking position, the nail 20 is attached with a first bone screw 48 through the open through-hole 60 and a second bone screw 48 through a distal end of the dynamization windows 44. The two screw attachment helps further secure the distal fragment 68 to the nail 20, and particularly helps to prevent any rotational movement or "toggling" of the distal fragment 68 which might otherwise occur about a single screw. Toggling of the distal fragment 68 may particularly be a problem if the distal end 26 of the nail 20 does not fit securely and tightly within the medullary canal of the distal fragment 68.

With two screw attachments and particularly with the screw 48 through the open through-hole 60, there is very little dynamization which is initially seen by the fracture. However, an intermittent operation may be performed after initial healing of the fracture in which the bone screw 48 through the open though-hole 60 is removed, resulting in the delayed dynamic configuration. With a single screw attachment through the distal end of the dynamization windows 44, compressive dynamization of the fracture will be achieved after the intermittent operation.

Figure 10:
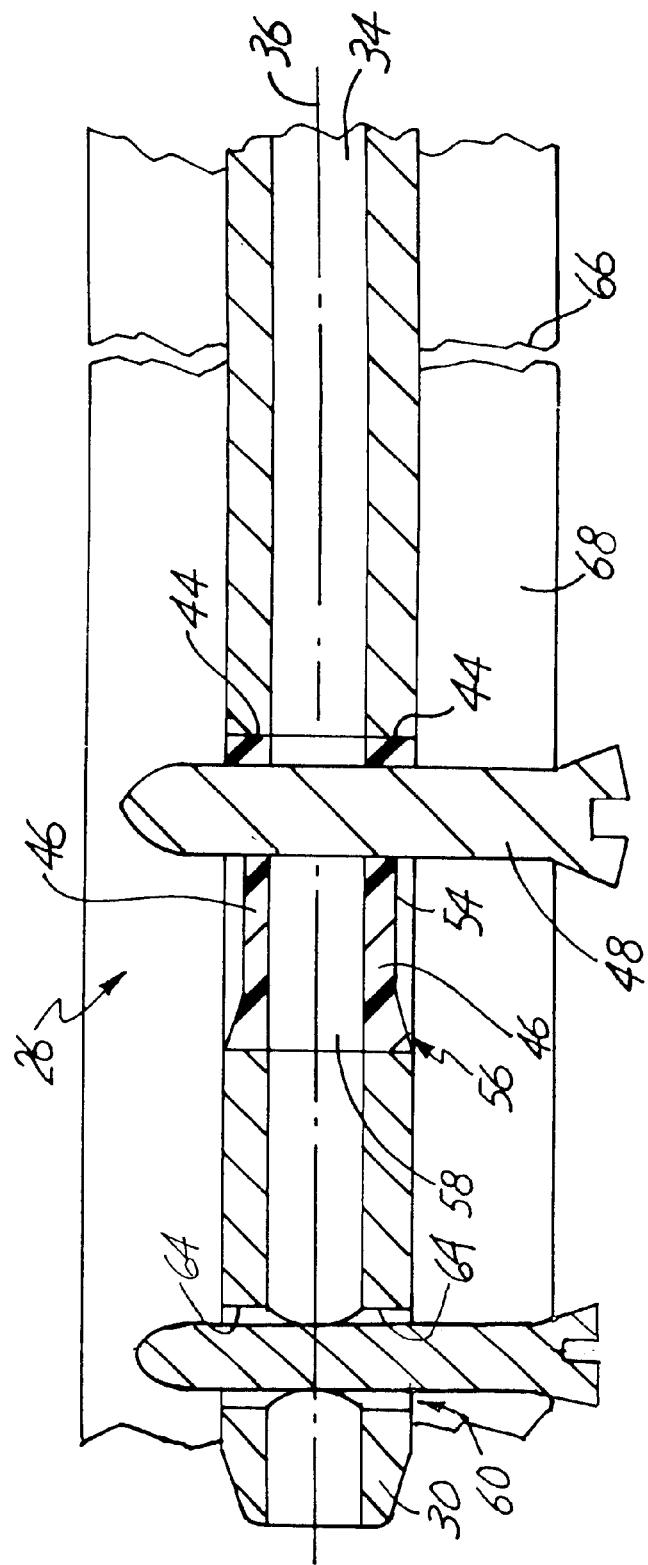
FIG. 10 is a cross-sectional view of a distal end of the nail of FIGS. 1–6 in a third type of attachment to a bone.

If a completely static attachment is desired, the recommended positioning of bone screws 48 includes a first screw 48 through the open through-hole 60 and a second bone screw 48 through a proximal end of the dynamization windows 44 as shown in FIG. 10. This positioning allows maximum separation between the bone screws 48 for toggle prevention and maximum strength. For each of the initial dynamic, the delayed dynamic and the completely static attachments, the surgeon can further adjust bone screw positioning as necessary for the condition of the bone.

In an alternative nail design (not shown) having two distal sets of dynamization windows 44, toggling of the distal fragment 68 will be prevented by a two screw attachment while full dynamization can be achieved without removal of either screw.

Many middle grounds or intermediate longitudinal locations can also be selected by the surgeon for placement of the bone screw 48 through the dynamization windows 44. By selecting the longitudinal location of the bone screw 48 through the dynamization windows 44, the surgeon can select the proportion of compressive dynamization and tensile dynamization seen at the fracture site 66.

The dynamization windows 44 are significantly longer than the width of the intended bone fastener 48. Because of this, while the exact longitudinal location of the bone fastener 48 is important for the desired dynamization, the exact longitudinal location is not critical to use of the nail 20. Minor longitudinal displacement errors of the bone fastener 48 will not prevent the bone fastener 48 from being advanced through the nail 20. The preferred nail structure 22 permits longitudinal displacement of the preferred bone fastener 48 up to a maximum of 0.434 inches while still receiving the bone fastener 48 through both windows 44. This large range of longitudinal location of the bone fastener 48 relative to the dynamization windows 44 not only provides permissible error for the surgeon, but also allows the surgeon flexibility in placement of the bone fasteners 48 relative to the fracture and relative to changes in bone condition at different longitudinal locations.

FIGS. 11–13 further show how the present invention provides flexibility in locating the bone fastener(s) 48 relative to the intramedullary nail 20 and also in providing for a range of error in locating the bone fastener(s) 48 relative to the nail 20. These benefits are achieved due to the different mechanical properties (such as hardness) of the non-metal material of the spacers 46, regardless of whether the non-metal material chosen is bioresorbable.

The longitudinal length of the two windows 44 with respect to each other allows for a significant longitudinal angulation $\gamma$ of the bone screw 48 relative to the nail 20, such as up to about 45° as shown in FIG. 11. Three factors may result in the longitudinal angulation $\gamma$ of the bone screw 48. Firstly, the location of the bone fastener 48 shown in FIG. 11 may result in a bending dynamization of the fracture site 66. The bone fastener 48 contacts the nail 20 at a proximal end 70 of one dynamization window 44 and at a distal end 72 of the other dynamization window 44. Tensile loads are transmitted through the distal end 72 contact without dynamization, and compressive loads are transmitted through the proximal end 70 contact without dynamization. However, bending stress such as that created by placing a clockwise (in FIG. 11) moment on the distal fragment 68 may allow dynamization. The extent of bending dynamization of the fracture site 66 depends on how secure the distal end 26 is in the medullary canal of the distal fragment 68. A loose fit of the distal end 26 in the distal fragment 68 will allow some rotational play, and the compressibility of the spacer material will govern how much bending stress is transferred through the fracture. Conversely, a tight fit of the distal end 26 in the distal fragment 68 will prevent any clockwise bending dynamization, as the distal fragment 68 cannot rotate relative to the nail 20 due to the tight fit. A loose fit of the distal end 26 in the distal fragment 68 may result either from the condition of the original bone or due to widening the medullary canal during surgery relative to the diameter of the nail 20. If the surgeon wishes clockwise bending dynamization to occur, first a loose fit must be obtained, and then the bone fastener 48 is placed through the dynamization windows 44 as shown in FIG. I1. Through proper longitudinal angulation $\gamma$ of the bone fastener 48, the structure of the preferred nail 20 thus allows the surgeon to select whether, how much, and in which direction bending dynamization occurs.

A second reason for longitudinal angulation $\gamma$ of the bone fastener 48 is based on the condition of the fracture. With longitudinal angulation $\gamma$ of the bone fastener 48, the bone fastener 48 extends through one side of the cortex at a position longitudinally offset from the location the bone fastener 48 extends through the other side of the cortex. The surgeon may determine that significant longitudinal angulation $\gamma$ is necessary for best securement of the bone fastener 48 relative to the fracture location(s).

A third reason for longitudinal angulation $\gamma$ of the bone fastener 48 is merely due to longitudinal angular misalignment of the bone fastener 48. The axis of the bone fastener 48 may be angularly misaligned relative to its desired position. The structure of the preferred nail 20 permits longitudinal angular misalignment of the bone fastener 48 while still receiving the bone fastener 48 through both windows 44.

As best shown in FIG. 12, the width of the two windows 44 is preferably greater than the width of the bone fastener 48. This difference in width permits some transverse displacement 74 of the bone screw 48 with respect to the longitudinal axis 36 of the nail 20, either by error or as intended by the surgeon. The structure of the preferred nail 20 in conjunction with the preferred bone fastener 48 permits a transverse displacement 74 up to a maximum of 0.071 inches. Because the spacer material is drilled in-situ or the bone fastener 48 used opens its own hole through the spacer 46, the spacer 46 holds the bone fastener 48 securely with respect to the nail 20 anywhere within the dynamization windows 44, at least until resorption of the spacer 46 becomes significant.

As best shown in FIG. 13, because the width of the windows 44 is greater than the width of the bone screw 48, some amount of transverse angulation $\delta$ is also permitted. Similar to transverse displacement 74, this transverse angulation $\delta$ may either be the result of error or be intended by the surgeon. The structure of the preferred nail 20 permits a transverse angulation $\delta$ with the preferred bone fastener 48 up to a maximum of about 11° from the axis of the dynamization windows 44.

The preferred PLA material for the spacers 46 and the preferred shape of the spacers 46 provide very useful general purpose dynamization characteristics based on currently known information about how bone fractures heal. The present invention further introduces an entirely new science to bone healing. That is, as explained with regard to the preferred embodiment, the selection of the bioresorbable material determines its compressibility curve as a function of resorption time. Different bioresorbable materials have different compressibility curves, affecting the dynamization seen at the fracture site 66. Different spacer geometries and different bone fastener locations and geometries also affect the dynamization (tensile, compressive and bending) seen at the fracture site 66. The present invention will allow a new body of data to be gathered on the effectiveness of bone fracture healing under different dynamization conditions. Based on this data, future changes may be made to further improve the invention, or to modify the invention for particular bone or fracture conditions. For instance, not only may a different bioresorbable material be used to change the compressibility curve, but a combination of bioresorbable materials may be used. Composite bioresorbable materials may be formed to combine compressibility characteristics, or the spacer(s) 46 may be formed of two or more distinct bioresorbable materials. The thickness of these two or more materials may be selected to engineer the desired compressibility curve of the spacer 46 and thereby provide the most beneficial dynamization characteristics. The bone fastener 48 may be positioned in the dynamization window 44 between a proximal spacer portion of one material and a distal spacer portion of a second material so as to have tensile dynamization characteristics which differ from compressive dynamization characteristics. The spacers 46 in opposing windows 44 may be of different sizes or formed of different bioresorbable materials to control the bending dynamization relative to the tensile and compressive dynamization. The present invention thus allows controlled dynamization across the fracture site 66, both for improving fracture healing and for learning more about how dynamization affects the healing of the fracture.

The preferred PLA material does not include any active agents for release during bioresorption. Alternatively, the bioresorbable material may include an active agent as desired for release adjacent the fracture site, such as an antibiotic or a growth factor.

Although the present invention has been described with reference to preferred embodiments, workers skilled in the art will recognize that changes may be made in form and detail without departing from the spirit and scope of the invention. For instance, while all of the these attachments methods have been described with regard to the preferred bicortical attachment, unicortical attachment can also be used with a shorter bone fastener or by only advancing the bone fastener partially through the nail 20.

What is claimed is:

1. An intramedullary nail for treatment of a fracture of a bone having a medullary canal extending longitudinally, comprising:
   a nail structure extending longitudinally and formed of metal, the nail structure having a distal end with a tip for insertion into the medullary canal and a proximal end opposite the distal end, with a first window defined in an exterior side of the distal end of the nail structure, the first window having a first window longitudinal length and a first window width not equal to the first window longitudinal length; and
   first spacer formed of a non-metal material which is slidably insertable to fit within the first window.

2. The intramedullary nail of claim 1, wherein the non-metal material of the first spacer is a bioresorbable material.

3. The intramedullary nail of claim 1, wherein the nail structure further comprises:
   a second window defined in an exterior side of the distal end of the nail structure opposing the first window permitting bicortical attachment with a bone fastener through the first and second windows, the second window having a second window longitudinal length and a second window width not equal to the second window longitudinal length.

4. The intramedullary nail of claim 3, wherein a second spacer formed of a non-metal material is within the second window.

5. The intramedullary nail of claim 4, wherein the nail structure further comprises a nail structure cannula defined longitudinally therein, wherein the first spacer and the second spacer are formed by a single insert with an insert cannula defined therethrough and aligned with the nail structure cannula.

6. The intramedullary nail of claim 3, wherein the nail structure includes a bend such that a longitudinal axis of the nail structure lies within a bisecting plane, and wherein the first window and the second window are symmetrically disposed on opposing sides of the bisecting plane.

7. The intramedullary nail of claim 1, wherein the first window longitudinal length is greater than the first window width.

8. The intramedullary nail of claim 1, wherein the nail structure further comprises a cannula defined longitudinally therein.

9. The intramedullary nail of claim 1, wherein the first spacer fills the first window prior to anchoring of a bone fastener.

10. The intramedullary nail of claim 1, wherein an additional bone attachment hole is defined in a proximal end of the nail structure.

11. The intramedullary nail of claim 1, wherein the nail structure includes an opening longitudinally spaced from the first window and in the distal end of the nail structure.

12. The intramedullary nail of claim 1,
   wherein the non-metal material of the first spacer is a bioresorbable material;
   wherein the first window longitudinal length is greater than the first window width;
   wherein the nail structure further comprises:
      a second window defined in an exterior side of the nail structure opposing the first window permitting bicortical attachment with the bone fastener through the first and second windows, the second window having a second window longitudinal length and a second window width less than the second window longitudinal length;
      a bend such that a longitudinal axis of the nail structure lies within a bisecting plane, wherein the first window and the second window are symmetrically disposed on opposing sides of the bisecting plane;
      a nail structure cannula defined longitudinally in the nail structure;
      a through-hole defined through the distal end of the nail structure and longitudinally spaced from the first and second windows; and
      an additional bone attachment hole defined in a proximal end of the nail structure; and
   wherein a bioresorbable insert provides the first spacer, the bioresorbable insert further providing a second spacer, the first spacer filling the first window and the second spacer filling the second window prior to anchoring a bone fastener through the first and second windows; and
   wherein an insert cannula is defined through the bioresorbable insert and aligned with the nail structure cannula.

13. An intramedullary nail assembly for treatment of a fracture of a bone having a medullary canal extending longitudinally, comprising;
   a nail structure extending longitudinally and formed of metal, the nail structure having a sidewall with a longitudinal bore extending from a distal end to a proximal end opposite the distal end, with a first window extending through said sidewall, the first window having a first window shape; and
   a first spacer formed of a non-metal material separately from the nail structure, the first spacer having outer dimensions which correspond to the first window shape, such that the first spacer is slidably insertable into the first window and received by the first window to secure the first spacer relative to the nail structure.

14. The intramedullary nail assembly of claim 13, wherein the nail structure is formed with a second window defined in an exterior side of the nail structure opposing the first window, the second window having a second window shape permitting bicortical attachment with a bone fastener through the first and second windows, and further comprising:

a second spacer formed of a non-metal material, the second spacer having outer dimensions which correspond to the second window shape, the first spacer and the second spacer being formed by a single insert which can be positioned into both the first and second windows from one side of the nail structure.

15. The intramedullary nail assembly of claim 14, wherein the nail structure further comprises a nail structure cannula defined longitudinally therein, wherein the single insert is formed with an insert cannula defined therethrough, the insert cannula sized and positioned in the single insert for alignment with the nail structure cannula when the single insert is positioned into the first and second windows of the nail structure.

16. The intramedullary nail assembly of claim 14, further comprising:

a bone fastener having a length sufficient to extend through the first and second windows in bicortical attachment with a bone, the bone fastener having a width small enough to be received in the first and second spacers within the first and second windows.

17. The intramedullary nail assembly of claim 16, wherein the bone fastener is a bone screw, and wherein the width and thickness of the bone fastener are equal diameters of the bone screw.

18. The intramedullary nail assembly of claim 13, wherein the outer dimensions of the first spacer are sized to be received in the first window with a press fit.

19. The intramedullary nail assembly of claim 13, wherein the first spacer fills the first window prior to anchoring of a bone fastener transversely through the first spacer.

20. The intramedullary nail assembly of claim 13, wherein the first window has a first window longitudinal length, wherein the first window is disposed in one of the distal end and the proximal end of the nail structure, wherein the nail structure has an opening defined in an exterior side of the nail structure in said one of the distal end and the proximal end, the opening being longitudinally spaced from the first window such that the first window and the opening are placed on the same side of the fracture, the opening having a longitudinal length which is less than the first window longitudinal length such that anchoring of a bone fastener transversely through the bone and into the opening can prevent dynamization while anchoring of a bone fastener transversely through the bone and into the first window can permit dynamization.

21. The intramedullary nail assembly of claim 13, wherein the non-metal material of the first spacer is a bioresorbable material.

22. The intramedullary nail assembly of claim 21, wherein the first window is machined into the nail structure with a first window longitudinal length and a first window width not equal to the first window longitudinal length, and wherein the first spacer is formed with a first spacer length corresponding to the first window longitudinal length, and a first spacer width corresponding to the first window width and not equal to the first spacer length.

23. The intramedullary nail assembly of claim 13, further comprising:

a second spacer formed of a non-metal material separately from the nail structure and separately from the first spacer, the second spacer having outer dimensions which correspond to the first window shape, such that the second spacer can be placed into and received by the first window to secure the second spacer relative to the nail structure, the second spacer having different mechanical or chemical treatment properties than the first spacer.

24. The intramedullary nail assembly of claim 23, wherein the different mechanical or chemical treatment properties are selected from the group consisting of: different hardness, different rates of absorption, different active agents and different amounts of active agents.

25. An intramedullary nail for treatment of a fracture of a bone having a medullary canal extending longitudinally, comprising:

a nail structure extending longitudinally and formed of metal, the nail structure having a distal end with a tip for insertion into the medullary canal and a proximal end opposite the distal end, with a first window defined in an exterior side of the nail structure; and a first spacer formed of a non-metal material within the first window, the first spacer having a surface contour exposed in the first window which is sloped inward toward a center of the first spacer.

26. An intramedullary nail assembly for treatment of a fracture of a bone having a medullary canal extending longitudinally, comprising:

a nail structure extending longitudinally and formed of metal, the nail structure having a distal end with a tip for insertion into the medullary canal and a proximal end opposite the distal end, the nail structure having at least one window defined in an exterior side of the nail structure for exposure of a selected spacer;

a first spacer formed of a non-metal material, the first spacer being sized such that it is received in the nail structure in an exposed position for transverse fastening through the nail structure and through the first spacer with a bone fastener; and a second spacer formed separately from the first spacer, the second spacer being sized such that it is received in the nail structure in an exposed position for transverse fastening through the nail structure and through the second spacer with a bone fastener, the second spacer having different mechanical or chemical treatment properties than the first spacer.

27. The intramedullary nail assembly of claim 26, wherein the different mechanical or chemical treatment properties are selected from the group consisting of: different hardness, different rates of absorption, different active agents and different amounts of active agents.

* * * * *

UNITED STATES PATENT AND TRADEMARK OFFICE
CERTIFICATE OF CORRECTION

PATENT NO. : 6,296,645 B1
DATED : October 2, 2001
INVENTOR(S) : Anne Hover et al.

It is certified that error appears in the above-identified patent and that said Letters Patent is hereby corrected as shown below:

Column 3,
Line 3, delete "materials", insert --material is --

Column 5,
Line 54, delete "dimenisioned", insert -- dimensioned --

Column 6,
Line 46, delete "showing", insert -- shows --

Column 10,
Line 20, delete "sort", insert -- short --

Column 11,
Line 61, delete FIG. I1.", insert -- "FIG. 11." --

Column 13,
Line 38, before "first", insert -- a --

Signed and Sealed this

Fourth Day of June, 2002

Attest:

Attesting Officer

JAMES E. ROGAN
Director of the United States Patent and Trademark Office